(12) United States Patent
Yanagawa

(10) Patent No.: US 9,196,843 B2
(45) Date of Patent: Nov. 24, 2015

(54) FULLERENE DERIVATIVE, AND METHOD OF PREPARING THE SAME

(71) Applicant: Yoshiki Yanagawa, Shizuoka (JP)

(72) Inventor: Yoshiki Yanagawa, Shizuoka (JP)

(73) Assignee: RICOH COMPANY, LTD., Tokyo (JP)

( * ) Notice: Subject to any disclaimer, the term of this patent is extended or adjusted under 35 U.S.C. 154(b) by 261 days.

(21) Appl. No.: 13/906,920

(22) Filed: May 31, 2013

(65) Prior Publication Data
US 2014/0024839 A1   Jan. 23, 2014

(30) Foreign Application Priority Data

Jul. 17, 2012  (JP) ................. 2012-159054
Apr. 8, 2013   (JP) ................. 2013-080186

(51) Int. Cl.
H01L 51/00   (2006.01)
C01B 31/02   (2006.01)
C07D 209/96  (2006.01)
H01L 51/42   (2006.01)

(52) U.S. Cl.
CPC ........ H01L 51/0067 (2013.01); *C01B 31/0213* (2013.01); *C07D 209/96* (2013.01); *H01L 51/0047* (2013.01); *H01L 51/0037* (2013.01); *H01L 51/4253* (2013.01); *H01L 2251/308* (2013.01)

(58) Field of Classification Search
None
See application file for complete search history.

(56) References Cited

FOREIGN PATENT DOCUMENTS

| JP | 2010-219448 | 9/2010 |
| JP | 2011-026235 | 2/2011 |
| JP | 2011-035116 | 2/2011 |
| JP | 2011-077486 | 4/2011 |
| JP | 2011-093848 | 5/2011 |
| JP | 2011-098906 | 5/2011 |
| JP | 2011-121886 | 6/2011 |

OTHER PUBLICATIONS

Grant & Hackh's Chemical Dictionary (5th Ed. 1987) at p. 148.*
Hong et al., Filled and glycosylated carbon nanotubes for in vivo radioemitter localization and imaging. Nature Materials, 2010, 9, 485-490.*
Aroua et al., Prato Reaction of M3N@Ih-C80 (M=Sc, Lu, Y, Gd) with Reversible Isomierzation. Journal of American Chemical Society, 2012, 134, 20242-20245.*

* cited by examiner

*Primary Examiner* — Michael Barker
*Assistant Examiner* — Po-Chih Chen
(74) *Attorney, Agent, or Firm* — Cooper & DUnham LLP

(57) ABSTRACT

A fullerene derivative having 60 or more carbon atoms includes at least one structure having the following formula (I):

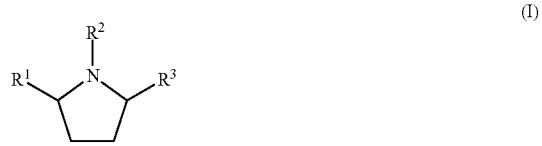

(I)

wherein $R^1$, $R^2$ and $R^3$ independently represent a hydrogen atom, a halogen atom, a substituted or unsubstituted alkyl group, a substituted or unsubstituted alkoxy group, a substituted or unsubstituted aryl group and a substituted or unsubstituted monofunctional heterocyclic group; and at least one of $R^1$, $R^2$ and $R^3$ comprises the following formula (II):

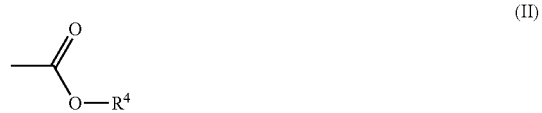

(II)

wherein $R^4$ represents a substituted or unsubstituted alkyl group having 4 to 30 carbon atoms, a substituted or unsubstituted alkenyl group having 4 to 30 carbon atoms, a substituted or unsubstituted alkynyl group having 4 to 30 carbon atoms or a substituted or unsubstituted aralkyl group having 4 to 30 carbon atoms.

2 Claims, 1 Drawing Sheet

| 6. NEGATIVE ELECTRODE |
|---|
| 5. ELECTRON TAKEOFF LAYER |
| 4. MIXED LAYER |
| 3. POSITIVE HOLE TAKEOFF LAYER |
| 2. POSITIVE ELECTRODE |
| 1. TRANSPARENT SUBSTRATE |

FULLERENE DERIVATIVE, AND METHOD OF PREPARING THE SAME

CROSS-REFERENCE TO RELATED APPLICATIONS

This patent application is based on and claims priority pursuant to 35 U.S.C. §119 to Japanese Patent Applications Nos. 2012-159054 and 2013-080186, filed on Jul. 17, 2012 and Apr. 8, 2013, respectively, in the Japan Patent Office, the entire disclosure of which is hereby incorporated by reference herein.

BACKGROUND

1. Technical Field

The present invention relates to a new fullerene derivative useful as an organic semiconductive material and a method of preparing the same.

2. Description of the Related Art

Organic semiconductive materials are well studied in an organic electronics field such as organic transistors and organic ELs. Further, an organic solar battery using a fullerene derivative as an organic photoelectric conversion element is strenuously studied. As the most famous fullerene derivative in this field, [6,6]-phenylC61-butyric methyl ester (PCBM) which is soluble in an organic solvent is disclosed in J. Org. Chem. 1995, 60, 532-538. A functional group having a suitable size is introduced to the fullerene and solubility in an organic solvent is adjusted to increase an area of a pn bonded interface which is a charge generation area and photoelectric conversion efficiency. However, the photoelectric conversion efficiency is still insufficient, and a better fullerene derivative is required.

Japanese published unexamined applications Nos. JP-2011-26235-A, JP-2011-35116-A, JP-2011-77486-A, JP-2011-93848-A, JP-2011-98906-A and JP-2011-121886-A disclose fullerene derivatives various functional groups are introduced to for the purpose of improving an open end voltage and expanding absorption wavelength area. Bulky functional groups are introduced to the fullerenes to improve solubility in an organic solvent and further, and further, compatibility with a p-type semiconductive material is increased to improve photoelectric conversion efficiency. However, the photoelectric conversion efficiency is still unsatisfactory.

Because of these reasons, a need exist for a fullerene derivative capable of providing high photoelectric conversion efficiency, the solubility in an organic solvent of which is controllable with an external stimulus.

SUMMARY

Accordingly, one object of the present invention is to provide a fullerene derivative capable of providing high photoelectric conversion efficiency, the solubility in an organic solvent of which is controllable with an external stimulus.

Another object of the present invention is to provide a method of preparing the fullerene derivative.

These objects and other objects of the present invention, either individually or collectively, have been satisfied by the discovery of a fullerene derivative having 60 or more carbon atoms, comprising at least one structure having the following formula (I):

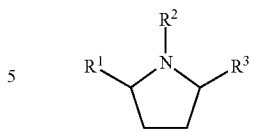

(I)

wherein $R^1$, $R^2$ and $R^3$ independently represent a hydrogen atom, a halogen atom, a substituted or unsubstituted alkyl group, a substituted or unsubstituted alkoxy group, a substituted or unsubstituted aryl group and a substituted or unsubstituted monofunctional heterocyclic group; and at least one of $R^1$, $R^2$ and $R^3$ comprises the following formula (II):

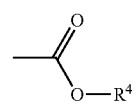

(II)

wherein $R^4$ represents a substituted or unsubstituted alkyl group having 4 to 30 carbon atoms, a substituted or unsubstituted alkenyl group having 4 to 30 carbon atoms, a substituted or unsubstituted alkynyl group having 4 to 30 carbon atoms or a substituted or unsubstituted aralkyl group having 4 to 30 carbon atoms.

In another aspect, the present invention provides a fullerene derivative having 60 or more carbon atoms, comprising at least one structure having the following formula (III):

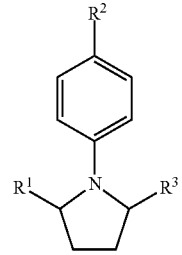

(III)

wherein. $R^1$, $R^2$ and $R^3$ independently represent a hydrogen atom, a halogen atom, a substituted or unsubstituted alkyl group, a substituted or unsubstituted alkoxy group, a substituted or unsubstituted aryl group and a substituted or unsubstituted monofunctional heterocyclic group; and at least one of $R^1$, $R^2$ and $R^3$ comprises the following formula (II):

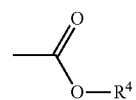

(II)

wherein $R^4$ represents a substituted or unsubstituted alkyl group having 4 to 30 carbon atoms, a substituted or unsubstituted alkenyl group having 4 to 30 carbon atoms, a substituted or unsubstituted alkynyl group having 4 to 30 carbon atoms or a substituted or unsubstituted aralkyl group having 4 to 30 carbon atoms.

In further aspect, the present invention provides a method of preparing a fullerene derivative having 60 or more carbon atoms, comprising at least one structure having the following formula (I):

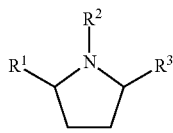

(I)

wherein $R^1$, $R^2$ and $R^3$ independently represent a hydrogen atom, a halogen atom, a substituted or unsubstituted alkyl group, a substituted or unsubstituted alkoxy group, a substituted or unsubstituted aryl group and a substituted or unsubstituted monofunctional heterocyclic group; and at least one of $R^1$, $R^2$ and $R^3$ comprises the following formula (II):

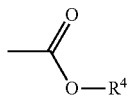

(II)

wherein $R^4$ represents a substituted or unsubstituted alkyl group having 4 to 30 carbon atoms, a substituted or unsubstituted alkenyl group having 4 to 30 carbon atoms, a substituted or unsubstituted alkynyl group having 4 to 30 carbon atoms or a substituted or unsubstituted aralkyl group having 4 to 30 carbon atoms, comprising:

reacting a precursor of the fullerene derivative having 60 or more carbon atoms, comprising at least one structure having the formula (I) with diethylpyrocarbonate having the following formula (V):

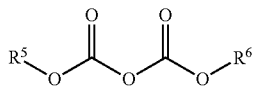

(V)

wherein $R^5$ and $R^6$ independently represent a substituted or unsubstituted alkyl group having 4 to 30 carbon atoms, a substituted or unsubstituted alkenyl group having 4 to 30 carbon atoms, a substituted or unsubstituted alkynyl group having 4 to 30 carbon atoms or a substituted or unsubstituted aralkyl group having 4 to 30 carbon atoms.

These and other objects, features and advantages of the present invention will become apparent upon consideration of the following description of the preferred embodiments of the present invention taken in conjunction with the accompanying drawings.

BRIEF DESCRIPTION OF THE DRAWINGS

Various other objects, features and attendant advantages of the present invention will be more fully appreciated as the same becomes better understood from the detailed description when considered in connection with the accompanying drawings in which like reference characters designate like corresponding parts throughout and wherein:

FIGURE is an embodiment of configuration of an organic solar battery.

DETAILED DESCRIPTION

The present invention provides a fullerene derivative capable of providing high photoelectric conversion efficiency, the solubility in an organic solvent of which is controllable with an external stimulus.

More particularly, the present invention relates to a fullerene derivative having 60 or more carbon atoms, comprising at least one structure having the following formula (I):

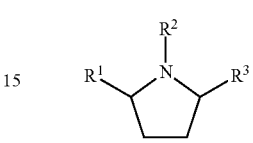

(I)

wherein $R^1$, $R^2$ and $R^3$ independently represent a hydrogen atom, a halogen atom, a substituted or unsubstituted alkyl group, a substituted or unsubstituted alkoxy group, a substituted or unsubstituted aryl group and a substituted or unsubstituted monofunctional heterocyclic group; and at least one of $R^1$, $R^2$ and $R^3$ comprises the following formula (II):

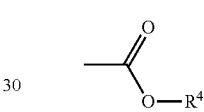

(II)

wherein $R^4$ represents a substituted or unsubstituted alkyl group having 4 to 30 carbon atoms, a substituted or unsubstituted alkenyl group having 4 to 30 carbon atoms, a substituted or unsubstituted alkynyl group having 4 to 30 carbon atoms or a substituted or unsubstituted aralkyl group having 4 to 30 carbon atoms.

A fullerene derivative including a functional group having the formula (II) has affinity with an organic solvent and is capable of changing solubility because the functional group resolves and releases due to an external stimulus such as a heat, light or a chemical means.

The fullerene of the present invention includes C60, C70, C76, C78, C80, C82, C84, C86, C88, C90, C92, C94, C96, etc.

The halogen atom in the formula (I) includes a fluorine atom, a chlorine atom, a bromine atom, and an iodine atom.

The substituted or unsubstituted alkyl group in the formula (I) has 1 to 30 carbon atoms, and may be straight-chain, branched-chain alkyl group or a cycloalkyl group. Specific examples of the alkyl group include methyl groups, ethyl groups, n-propyl groups, i-propyl groups, n-butyl groups, i-butyl groups, tert-butyl groups, sec-butyl groups, 3-methylbutyl groups, n-pentyl groups, n-hexyl groups, 2-ethylhexyl groups, n-heptyl groups, n-octyl groups, n-nonyl groups, n-decyl groups and n-lauryl groups. The alkyl group may have a substituent, and specific examples of the substituent include, besides the substituents having the formula (II), alkyl groups having 1 to 12 carbon atoms such as hydroxy groups, methyl groups, ethyl groups, tert-butyl groups and octyl groups; aryl groups having 6 to 12 carbon atoms such as phenyl groups, naphtyl groups and phenyl groups; aralkyl groups having 7 to 12 carbon atoms such as benzyl groups; acyl groups having 2 to 2 carbon atoms such as glycidyloxy groups and acetyl groups; acyloxy groups having 1 to 12 carbon atoms such as acetyloxy group; amino groups substituted with alkyl groups having 1 to 12 carbon atoms such as amino groups, methylamino groups, ethylamino groups and dimethylamino groups; halogen groups (halogen atoms) such as fluoro groups (fluorine atoms), chloro groups (chlorine atoms) and bromo groups (bromine atoms); oxo groups (=O); and carboxy groups (—COOH). These substituents may be residual groups having the substituents having the formula (II).

The substituted or unsubstituted alkoxy group in the formula (I) has 1 to 30 carbon atoms, and may be straight-chain, branched-chain alkyl group or a cycloalkyl group. Specific examples of the alkoxy group include methoxy groups, ethoxy groups, n-propyloxy groups, i-propyloxy groups, n-butoxy groups, i-butoxy groups, sec-butoxy groups, tert-butoxy groups, n-pentyloxy groups, n-hexyloxy groups, cyclohexyloxy groups, n-heptyloxy groups, n-octyloxy groups, 2-ethylhexyloxy groups, n-nonyloxy groups, n-decyloxy groups, 3,7-dimethyloxyloxy groups and n-lauryloxy groups. The alkoxy group may have a substituent, and specific examples of the substituent include, besides the substituents having the formula (II), the same substituents of the alkyl groups. These substituents may be residual groups having the substituents having the formula (II).

The substituted or unsubstituted aryl group in the formula (I) has 6 to 60 carbon atoms, and specific examples thereof include phenyl groups, alkylphenyl groups, alkoxyphenyl groups, 1-naphtyl groups and 2-naphtyl groups. The aryl group may have a substituent, and specific examples of the substituent include, besides the substituents having the formula (II), the same substituents of the alkyl groups. These substituents may be residual groups having the substituents having the formula (II).

The substituted or unsubstituted monofunctional heterocyclic group in the formula (I) has at least one nitrogen atom, one oxygen atom or one sulfur atom in its ring, and the one ring has 5 to 20 members. Specific examples thereof include pyridyl groups, thienyl groups, phenylthienyl groups, thiazolyl groups, furyl groups, piperidyl groups, piperazyl groups, pyrrolyl groups, morpholino groups, imidazolyl groups, indolyl groups, quinolyl groups, and pyrimidinyl groups. The monofunctional heterocyclic group may have a substituent, and specific examples of the substituent include, besides the substituents having the formula (II), the same substituents of the alkyl groups. These substituents may be residual groups having the substituents having the formula (II).

The alkyl group in the formula (II) includes the same alkyl groups in the formula (I).

The substituted or unsubstituted alkenyl group in the formula (II) is the alkyl group having two or more carbon atoms and at least one double bond. Specific examples thereof include vinyl groups, allyl groups, 1-propenyl groups, isopropenyl groups, 2-butenyl groups, 1,3-butandienyl groups, 2-pentenyl groups, 2-hexenyl groups, cyclopentenyl groups and cyclohexenyl groups. The alkenyl group may have a substituent, and specific examples of the substituent include the same substituents of the alkyl groups.

The substituted or unsubstituted alkynyl group in the formula (II) is the alkyl group having two or more carbon atoms and at least one triple bond. Specific examples thereof include ethynyl groups, 1-propynyl groups and 2-propynyl groups. The alkynyl group may have a substituent, and specific examples of the substituent include the same substituents of the alkyl groups.

The aralkyl group in the formula (II) has 7 to 30 carbon atoms, and specific examples thereof include benzyl groups, phenetyl groups, naphthylmethyl groups and naphtyl ethyl groups. The aralkyl group may have a substituent, and specific examples of the substituent include the same substituents of the alkyl groups.

The halogen atom, alkyl group, alkoxy group, aryl group, monofunctional heterocyclic group, alkenyl group, alkynyl group an aralkyl group in the formulae (III) to (V) are the same in the formulae (I) to (II).

Specific examples of the functional groups of $R^1$, $R^2$ and $R^3$ in the formulae (I), (III) and are shown in Tables 1-1 to 1-8.

TABLE 1-1

| No. | $R^1$ | $R^2$ | $R^3$ |
|---|---|---|---|
| 1 | —H | (4-(tert-butoxycarbonyloxy)phenyl) | —H |
| 2 | —H | (4-(tert-butoxycarbonyloxy)phenyl) | —CH$_3$ |
| 3 | —H | (4-(tert-butoxycarbonyloxy)phenyl) | —CH$_2$CH$_3$ |
| 4 | —H | (4-(tert-butoxycarbonyloxy)phenyl) | —CH$_2$CH$_2$CH$_3$ |
| 5 | —H | (4-(tert-butoxycarbonyloxy)phenyl) | —CH(CH$_3$)$_2$ |
| 6 | —H | (4-(tert-butoxycarbonyloxy)phenyl) | —CH$_2$CH$_2$CH$_2$CH$_3$ |
| 7 | —H | (4-(tert-butoxycarbonyloxy)phenyl) | —C(CH$_3$)$_3$ |
| 8 | —H | (4-(tert-butoxycarbonyloxy)phenyl) | —CH=CHCH$_3$ |
| 9 | —H | (4-(tert-butoxycarbonyloxy)phenyl) | —CH$_2$CH$_2$CH$_2$CH$_2$CH$_3$ |

TABLE 1-2

| No. | R¹ | R² | R³ |
|-----|----|----|----|
| 10 | —H | 4-methylphenyl tert-butyl carbonate | penta-2,4-dien-1-yl (CH₃ terminated) |
| 11 | —H | 4-methylphenyl tert-butyl carbonate | n-heptyl (CH₃) |
| 12 | —H | 4-methylphenyl tert-butyl carbonate | n-octyl (CH₃) |
| 13 | —H | 4-methylphenyl tert-butyl carbonate | n-nonyl (CH₃) |
| 14 | —H | 4-methylphenyl tert-butyl carbonate | n-decyl (CH₃) |
| 15 | —H | 4-methylphenyl tert-butyl carbonate | n-undecyl (CH₃) |
| 16 | —H | 4-methylphenyl tert-butyl carbonate | n-dodecyl (CH₃) |
| 17 | —H | 4-methylphenyl tert-butyl carbonate | n-tridecyl (CH₃) |
| 18 | —H | 4-methylphenyl tert-butyl carbonate | n-tetradecyl (CH₃) |

TABLE 1-3
| No. | R¹ | R² | R³ |
|---|---|---|---|
| 19 | —H |  |  |
| 20 | —H |  |  |
| 21 | —H |  |  |
| 22 | —H |  |  |
| 23 | —H |  |  |
| 24 | —H |  |  |
| 25 | —H |  |  |
| 26 | —H |  |  |
TABLE 1-4
| No. | R¹ | R² | R³ |
|---|---|---|---|
| 27 | —H |  |  |
| 28 | —H | 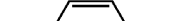 |  |
| 29 | —H |  |  |
| 30 | —H |  | |
| 31 | —H | | |

TABLE 1-4-continued

| No. | R¹ | R² | R³ |
|---|---|---|---|
| 32 | —H | 4-(tert-butoxycarbonyloxy)phenyl | 4-(dimethylamino)phenyl |
| 33 | —H | 4-(tert-butoxycarbonyloxy)phenyl | 4-nitrophenyl |
| 34 | —H | 4-(tert-butoxycarbonyloxy)phenyl | 4-ethoxyphenyl |
| 35 | —H | 4-(tert-butoxycarbonyloxy)phenyl | 4-propoxyphenyl |

TABLE 1-5

| No. | R¹ | R² | R³ |
|---|---|---|---|
| 36 | —H | 4-(tert-butoxycarbonyloxy)phenyl | 3,5-dimethoxy-4-hydroxyphenyl |
| 37 | —H | 4-(tert-butoxycarbonyloxy)phenyl | 4-(trifluoromethoxy)phenyl |
| 38 | —H | 4-(tert-butoxycarbonyloxy)phenyl | 4-((tert-butyldimethylsilyl)oxy)phenyl |

TABLE 1-5-continued

| No. | R¹ | R² | R³ |
|-----|----|----|----|
| 39 | —H | 4-(tert-butoxycarbonyloxy)phenyl | 4-(diphenylamino)phenyl |
| 40 | —H | 4-(tert-butoxycarbonyloxy)phenyl | pyridin-4-yl |
| 41 | —H | 4-(tert-butoxycarbonyloxy)phenyl | pyridin-2-yl |
| 42 | —H | 4-(tert-butoxycarbonyloxy)phenyl | 5-bromopyridin-2-yl |
| 43 | —H | 4-(tert-butoxycarbonyloxy)phenyl | 6-methoxypyridin-3-yl |
| 44 | —H | 4-(tert-butoxycarbonyloxy)phenyl | 6-bromopyridin-3-yl |

TABLE 1-6

| No. | R¹ | R² | R³ |
|-----|----|----|----|
| 45 | —H | 4-(tert-butoxycarbonyloxy)phenyl | 4-(benzyloxy)phenyl |
| 46 | —H | 4-(tert-butoxycarbonyloxy)phenyl | 4-phenoxyphenyl |

TABLE 1-6-continued

| No. | R¹ | R² | R³ |
|---|---|---|---|
| 47 | —H | 4-(tert-butoxycarbonyloxy)phenyl | 4-(4-methylphenoxy)phenyl |
| 48 | —H | 4-(tert-butoxycarbonyloxy)phenyl | 4-(4-fluorophenoxy)phenyl |
| 49 | —H | 4-(tert-butoxycarbonyloxy)phenyl | 4-(4-chlorophenoxy)phenyl |
| 50 | —H | 4-(tert-butoxycarbonyloxy)phenyl | 4-(4-nitrophenoxy)phenyl |
| 51 | —H | 4-(tert-butoxycarbonyloxy)phenyl | 4-(4-bromophenoxy)phenyl |
| 52 | —H | 4-(tert-butoxycarbonyloxy)phenyl | 4-(4-trifluoromethylphenoxy)phenyl |
| 53 | —H | 4-(tert-butoxycarbonyloxy)phenyl | biphenyl-4-yl |

TABLE 1-7

| No. | R¹ | R² | R³ |
|---|---|---|---|
| 54 | —H | 4-(tert-butoxycarbonyloxy)phenyl | 4'-methylbiphenyl-4-yl |

TABLE 1-7-continued

| No. | R¹ | R² | R³ |
|---|---|---|---|
| 55 | —H | 4-(tert-butoxycarbonyloxy)phenyl | diphenylmethyl |
| 56 | —H | 4-(tert-butoxycarbonyloxy)phenyl | 2-thienyl |
| 57 | —H | 4-(tert-butoxycarbonyloxy)phenyl | 2-naphthyl |
| 58 | —H | 4-(tert-butoxycarbonyloxy)phenyl | 1-naphthyl |
| 59 | —H | 4-(tert-butoxycarbonyloxy)phenyl | 5-acenaphthyl |
| 60 | —H | 4-(tert-butoxycarbonyloxy)phenyl | 2-fluorenyl |
| 61 | —H | 4-(tert-butoxycarbonyloxy)phenyl | 4-dibenzofuranyl |
| 62 | —H | 4-(tert-butoxycarbonyloxy)phenyl | 9-anthracenyl |

TABLE 1-8

| No. | R¹ | R² | R³ |
| --- | --- | --- | --- |
| 63 | —H | (4-tert-butoxycarbonyloxyphenyl)methyl | phenanthrenyl |
| 64 | —H | (4-tert-butoxycarbonyloxyphenyl)methyl | (9-ethylcarbazol-3-yl)methyl |
| 65 | —H | (4-tert-butoxycarbonyloxyphenyl)methyl | pyrenyl |

Each of the formulae (I) and (III) has one structural unit in the above Tables, and may have plural structural units, e.g., 2 to 4. Relative positions of the plural structural units are not limited.

An embodiment of the fullerene derivative of the present invention is synthesized by reacting a glycin derivative with an aldehyde derivative to produce azomethine ylide; adding the azomethine ylide to fullerene through Prato reaction (J. Am. Chem. SOC. 1993, 115, 9787-9799) to synthesize a fullero pyrrolidine derivative; and reacting the fullero pyrrolidine derivative with diethylpyrocarbonate having the formula (V) in a non-proton organic solvent under the presence of a base as a catalyst as disclosed in Japanese published unexamined application No. JP-2009-7523-A.

Specific examples of the glycin derivative include N-methoxymethylglycin, N-(2-(2-methoxyethoxy)ethyl)glycin, N-(4-hydroxyphenyl)glycin, etc.

An amount of the glycin derivative used is preferably from 0.1 to 10 mol, and more preferably from 0.5 to 5 mol per 1 mol of fullerene.

Specific examples of the aldehyde derivative include saturated or unsaturated aliphatic aldehyde, saturated or unsaturated alicyclic aldehyde, aromatic aldehyde, aldehyde including a heterocyclic ring, etc., and any of them may have a functional group.

The saturated or unsaturated aliphatic aldehyde has 1 to 30 carbon atoms, and may be straight-chain or a branched-chain aliphatic aldehyde. Specific examples thereof include formaldehyde, acetoaldehyde, propionaldehyde, isobutylaldehyde, butylaldehyde, trans-2-pentenal, valeraldehyde, trimethylacetoaldehyde, trans, trans-2,4-hexadienal, hexanal, 2-methylpentanal, heptoaldehyde, octanal, trans-2,cis-6-nonadienal, nonanal, decanal, aldehydeundecylenate, dodecanal, dodecylaldehyde, tridecanal, etc. The aliphatic aldehyde may have a substituent, and specific examples of the substituent include the same substituents of the alkyl groups.

The saturated or unsaturated alicyclic aldehyde has 1 to 30 carbon atoms, and may be straight-chain or a branched-chain alicyclic aldehyde. Specific examples thereof include cyclopropanecarboxyaldehyde, cyclopentanecarboxyaldehyde, cyclohexanecarboxyaldehyde, cycloheptanecarboxyaldehyde, cyclooctanecarboxyaldehyde, 3-cyclohexene-1-carboxyaldehyde, etc. The alicyclic aldehyde may have a substituent, and specific examples of the substituent include the same substituents of the alkyl groups.

The aromatic aldehyde has 6 to 60 carbon atoms, and includes benzaldehydes, benzyloxyaldehydes, phenoxybenzaldehydes, biphenylaldehydes, diphenylaldehydes, naphthoaldehydes, fluorenealdehydes, anthracenealdehydes, phenanthrenealdehydes, pyrenealdehydes, piperazinealdehydes, etc. Specific examples thereof include benzaldehyde, phenylacetoaldehyde, p-tolualdeyde, 4-fluorobennzaldehyde, 4-(dimethylamino)benzaldehyde, 4-formylphenyl boronic acid, 4-ethoxybenzaldehyde, 4-nitrobenzaldehyde, 4-tert-butylbenzaldehyde, 4-formylmethylbenzoate, 4-propoxybenzaldehyde, 4-(difluoromethoxy)benzaldehyde, 4-(1H-imidazole-1-yl)benzaldehyde, 4-nutoxybenzaldehyde, 4-(tert-butyloxy)benzaldehyde, syringaldehyde, 4-(2-pyridyl)benzaldehyde, 4-(trifluoromethoxy)benzaldehyde, 4-(pentyloxy)benzaldehyde, 4-(trifluoromethylthio)benzaldehyde, 4-(hexyloxy)benzaldehyde, 4-(diethoxymethyl)benzaldehyde, 4-butoxy-3-methoxy-benzaldehyde, 4-[N,N-bis(2-hydroxyethyl)amino]benzaldehyde, 4-(4-methylphenoxy)benzaldehyde, 4-(4-fluorophenoxy)benzaldehyde, 3,5,-di-tert-butylbenzaldehyde, 4-(heptyloxy)benzaldehyde, 4-(Boc-amino)benzaldehyde, 4-(1,1,2,2-tetrafluoroethoxy)benzaldehyde, 4-butoxy-3-ethoxybenzaldehyde, 4-(4-methoxyphenoxy)benzaldehyde, 4-(hexyloxy)-M-anisaldehyde, 4-[(tert-butyldimethylsylil)oxy]benzaldehyde, 3,5-bis(trifluoromethyl)benzaldehyde, 3,4-dibutoxybenzaldehyde, 4-(heptyloxy)-M-anisaldehyde, 4-(decyloxy)benzaldehyde, 4-(octyloxy)-M-anisaldehyde, 3-[3-(trifluoromethyl)phenoxy]benzaldehyde, 4-(diphenylamino)benzaldehyde, 4-(decyloxy)-M-anisaldehyde, 3,4-dibenzyloxybenzaldehyde, 4-(hexadecyloxy)benzaldehyde, 4-octadecyloxy-benzaldehyde, 4-hexadecyloxy-M-anisaldehyde, 4-(4,4,5,5,6,6,7,7,8,8,9,9,10,10,11,11-heptadecafluoroundecyloxy)benzaldehyde, biphenyl-4-carboxyaldehyde, biphenyl-3-carboxyaldehyde, 4-(4-methylphenyl)benzaldehyde, 3-(4-methylphenyl)benzaldehyde, diphenylacetoaldehyde, β-phenylcinnamaldehyde, 2-naphthoaldehyde, 1-naphthoaldehyde, 4-methyl-1-naphthoaldehyde, 5-acenaphthenecarboxyaldehyde, fluorene-2-carboxyaldehyde, 9-anthracenecarboxyaldehyde, 9-phenanthrenecarboxyaldehyde, 1-pyrenecarboxyaldehyde, 10-chloro-9-anthraaldehyde, tert-butyl-4-formylphenylcarbonate, 1-Boc-4-(2-formylphenyl)piperazine, etc. The aromatic aldehyde may have a substituent, and specific examples of the substituent include the same substituents of the alkyl groups.

The aldehyde including a heterocyclic ring has 5 o 20 members in one ring, and includes furaldehydes, pyridine aldehydes, thiophene aldehydes.

Specific examples thereof include 3-furancarboxyaldehyde, 2-furaldehyde, 5-methylfurfural, 5-hydroxymethyl-2-furaldehyde, 5-(hydroxymethyl)furfural, 5-nitro-2-furaldehyde, 5-phenyl-2-furaldehyde, 5-bromo-2-furaldehyde, 2-pyridinecarboxyaldehyde, 4-pyridinecarboxyaldehyde, 3-pyridinecarboxyaldehyde, 2-amino-3-pyridinecarboxyaldehyde, 6-methoxy-3-pyridinecarboxyaldehyde, 5-bromo-2-pyridinecarboxyaldehyde, 6-bromo-3-pyridinecarboxyaldehyde, 2-thiophenecarboxyaldehyde, dibenzofuran-4-carboxyaldehyde, 9-ethyl-3-carbazolecarboxyaldehyde, etc. The aldehyde including a heterocyclic ring may have a substituent, and specific examples of the substituent include the same substituents of the alkyl groups.

An amount of the aldehyde derivative used is preferably from 0.1 to 10 mol, and more preferably from 0.5 to 5 mol per 1 mol of fullerene.

In the Prato reaction, an organic solvent can be used. Specific examples thereof include toluene, benzene, hexane, cyclohexane, octane, xylene, chlorobenzene, carbon tetrachloride, 1-chloronaphthalene, etc. An amount of the organic solvent used is preferably from 1 to 100,000 times of the weight of fullerene.

Specific examples of the method of synthesizing the fullerene derivative include mixing fullerene, a glycin derivative and an aldehyde derivative, and heating them in an organic solvent at 50 to 350° C. for 30 min to 50 hrs. After heated, the reactant mixture is cooled to have room temperature, and the solvent is removed by a rotary evaporator under reduced pressure. Further, the resultant solid is separated and refined by silica gel flash column chromatography to prepare fullero pyrrolidine which is a material of the fullerene derivative.

Next, the fullero pyrrolidine derivative is reacted with diethylpyrocarbonate having the formula (V) in a non-proton organic solvent under the presence of a base as a catalyst as disclosed in Japanese published unexamined application No. JP-2009-7523-A to prepare an embodiment of the fullerene derivative of the present invention.

Specific examples of the non-proton organic solvent include ether solvents such as tetrahydrofuran and dioxane, glycol ether solvents such as ethyleneglycolmethylether and ethyleneglycolethylether, acetonitrile, N,N-dimethylformaldehyde, N,N-dimethylacetoamide, ethylcellosolve, ethylacetate, methylacetate, dichloromethane, monochlorobenzene, toluene, xylene, nitrobenzene, pyridine, picoline, quinoline, etc. The organic solvents used in the Prato reaction can also be used. An amount of the non-proton organic solvent used is preferably from 1 to 100,000 times of the weight of fullerene.

The base used as a catalyst includes alkali metals, and their hydrides and carbonates such as sodium and potassium; alkali metal amides such as sodium amides and potassium amides; and hydrogenated alkali metals such as hydrogenated lithium. As organic aliphatic bases, aromatic bases and heterocyclic N-bases, diazabicyclooctene, diazabicycloundecene, 4-dimethylaminopyridine, dimethylpyridine, pyridine, triethylamine, etc. An amount of the base used is preferably from 0.01 to 10 mol, and more preferably from 0.5 to 1 mol per 1 mol of fullerene.

The diethylpyrocarbonate having the formula (V) can be prepared by known methods, and is commercially available. $R^5$ and $R^6$ independently represent a substituted or unsubstituted alkyl group having 4 to 30 carbon atoms, a substituted or unsubstituted alkenyl group having 4 to 30 carbon atoms, a substituted or unsubstituted alkynyl group having 4 to 30 carbon atoms or a substituted or unsubstituted aralkyl group having 4 to 30 carbon atoms. The alkyl group is preferably used because of having a branched structure capable of noticeably improving solubility. An amount of the diethylpyrocarbonate having the formula (V) used is preferably from 0.1 to 20 mol, and more preferably from 0.5 to 10 mol per 1 mol of fullerene.

The solubility of the fullerene derivative of the present invention in an organic solvent can be reduced with an outer stimulus such as chemical means, heating means and photolytic means. This is because a functional group in the formula (H) of the fullerene derivative is decarboesterified by the outer stimulus to decrease a bulk of the pyrrolidine ring in the fullerene derivative. When the solubility in an organic solvent is controlled, the fullerene derivative can have a precise domain structure conventional fullerene derivatives have been unable to have. As a result, the fullerene derivative is effectively used in an organic electronics field where the domain structure thereof has an important role. Specifically, the fullerene derivative is dissolved in an organic solvent to prepare a solution, and the solution is coated as a coating liquid.

Next, the chemical means, the heating means and the photolytic means as an outer stimulus are explained in detail.

The chemical means includes a method of using a catalyst such as an acid or a base with no solvent or under the presence of a solvent. The catalyst is preferably an acid such as ethylacetate, trifluoromethylacetate, a propionic acid, an acrylic acid, a benzoic acid, a hydrochloric acid, a sulfuric acid, a boric acid, a p-toluenesulfonic acid, a salicylic acid, etc.

The heating means includes a method of heating at 50 to 300° C. with no solvent or under the presence of a solvent. The heating temperature is preferably from 70 to 250° C., and the heating time is preferably from 1 min to 20 hrs.

The photolytic means includes a method of irradiating light having a wavelength range the fullerene derivative of the present invention absorbs with no solvent or under the presence of a solvent. Specific examples of the light source include a high or a low pressure mercury lamp, a tungsten lamp, an LED lamp, a laser beam source, etc.

Specific examples of the solvent include ether solvents such as tetrahydrofuran and dioxane, glycol ether solvents such as ethyleneglycolmethylether and ethyleneglycolethylether, butanol, N,N-dimethylformaldehyde, N,N-dimethylacetoamide, ethylcellosolve, ethylacetate, butylacetate, monochlorobenzene, dichlorobenzene, toluene, xylene, anisole, cyclohexanone, nitrobenzene, pyridine, picoline, quinoline, etc.

Combinations of the chemical means, the heating means and the photolytic means can control the solubility more efficiently. Particularly, a combination of the chemical means and the heating means can efficiently control the solubility.

The fullerene derivative of the present invention can be used as an organic semiconductive material for organic transistors, organic ELs, organic solar batteries, etc. Organic semiconductive devices obtained from the fullerene derivative of the present invention can be prepared according to methods known in technical fields they belong to. Particularly, the fullerene derivative of the present invention is a promising organic semiconductive material for the organic solar batteries, and an embodiment thereof is explained.

FIGURE is an embodiment of configuration of an organic solar battery. The organic solar battery is formed by the following method. A positive electrode of, e.g., an electroconductive metal material is formed on a transparent substrate such as glasses. The positive electrode is formed by vacuum evaporation methods, etc. Next, a positive hole takeout layer is formed on the positive electrode when necessary. The positive hole takeout layer is formed by coating methods, etc., using a p-type semiconductive material. The positive hole takeout layer is preferably subjected to an annealing treatment exposing the layer to a solvent vapor under a solvent atmosphere or an annealing treatment heating the layer when necessary. A mixed layer formed of a p-type semiconductive material and an n-type semiconductive material, including at least the fullerene derivative of the present invention is formed on the positive hole takeout layer.

The mixed layer is formed by coating. The mixed layer is preferably subjected to an annealing treatment with a solvent or heat as well. The fullerene derivative of the present invention is capable of releasing the functional group having the formula (II) when heated to reduce solubility. Therefore, the annealing treatment with heat is preferably used. The heating temperature is preferably from 50 to 300° C., and the heating time is preferably from 1 min to 20 hrs. When the annealing treatment with heat positively reduces solubility of the fullerene derivative, the size of the domain thereof can be controlled. Therefore, a fine p/n bonded interface unformable with conventional fullerene derivatives can be formed to realize high incident photon-to-current conversion efficiency.

Next, an electron takeout layer is formed on the mixed layer. The electron takeout layer is formed by dry or wet film forming methods with an n-type semiconductive material. The electron takeout layer is preferably subjected to the annealing treatment with a solvent or a heat as well. The positive hole takeout layer and the electron takeout layer are formed when necessary, and may not be formed. Next, a negative electrode is formed on the electron takeout layer. The negative electrode is formed by vacuum evaporation methods, etc. as the positive electrode is.

EXAMPLES

Having generally described this invention, further understanding can be obtained by reference to certain specific examples which are provided herein for the purpose of illustration only and are not intended to be limiting. In the descriptions in the following examples, the numbers represent weight ratios in parts, unless otherwise specified.

Example 1

Synthesis Example of the Fullerene Derivative No. 1 in Table 1 (One Structural Unit Having the Formula (I)

[Step 1; Synthesis of Fullero Pyrrolidine]

Fullerene $C_{60}$ (250 mg, 0.35 mmol), N-(4-hydroxyphenyl) glycin (585 mg, 3.50 mmol), paraformaldehyde (50 mg, 1.77 mmol) and chlorobenzene (100 mL) were placed in a 200-mL double-necked flask equipped with Gimroth condenser, and heated to reflux for 3 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator. The product was reprecipitated with methanol (50 mL) to form a brown solid (100 mg).

The brown solid was subjected to IR absorption spectrum measurement, LC-MS and element analysis. The results are as follows.

IR Absorption Spectrum Measurement (KBr Tablet Method)

An absorption of OH stretching oscillation was observed at 3,440 $cm^{-1}$

LC-MS (Developing Solvent: Toluene)
  m/z=855.80 (theoretical value: 855.81)
Element Analysis
  C=95.4% (theoretical value: 95.43%)
  H=1.0% (theoretical value: 1.06%)
  N=1.7% (theoretical value: 1.64%)

From the above, the brown solid was found to be fullero pyrrolidine having the following formula (1) (yield rate 33.7%):

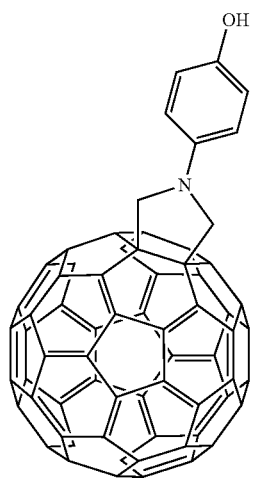

(1)

[Step 2; Synthesis of the Fullerene Derivative No. 1 in Table 1 (One Structural Unit Having the formula (I)]

The fullero pyrrolidine (100 mg, 0.12 di-tert-butyl dicarbonate (260 mg, 1.19 mmol), 4-dimethylaminopyridine (130 mg, 1.06 mmol) and pyridine (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator. The product was reprecipitated with methanol (50 mL) to form a brown solid (90 mg).

The brown solid was subjected to IR absorption spectrum measurement, LC-MS and element analysis. The results are as follows.

IR Absorption Spectrum Measurement (KBr Tablet Method)

The absorption of OH stretching oscillation was observed at 3,440 $cm^{-1}$ disappeared, an absorption of C—H stretching oscillation and an absorption of C=O stretching oscillation were observed at 2,920 $cm^{-1}$ and 1,750 $cm^{-1}$, respectively.

LC-MS (Developing Solvent: Toluene)
  m/z=955.80 (theoretical value: 955.92)
Element Analysis
  C=91.4% (theoretical value: 91.72%)
  H=1.8% (theoretical value: 1.79%)
  N=1.6% (theoretical value: 1.47%)

From the above, the brown solid was found to be a fullerene derivative No. 1 having the following formula (1a) (yield rate 69.4%):

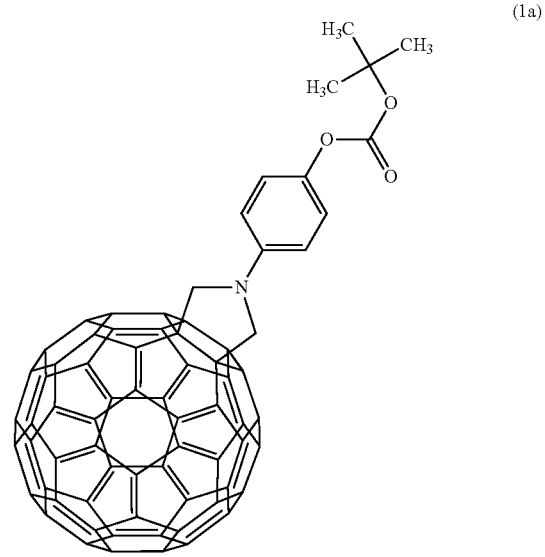 [SMILES: CC(C)(C)OC(=O)Oc1ccc(N2CC34C5=c6c7c8c9c%10c%11c%12c%13c%14c%15c%16c%17c(c6c(c%16%13)c%117)C3(C2)C2C%173CC26c2c7c%11c%13c%16c2c2c%17c%18c%19c%20c%21c%22c%23c(c-%13c%21c%18%16)C(C%14C%23C%12C%10C%22C%20C9C9C8C5C(C%17C%199)C4C26)C%11C%15C73)cc1]

(1a)

Example 2

Synthesis Example of the Fullerene Derivative No. 6 in Table 1 (One Structural Unit Having the Formula (I)

[Step 1; Synthesis of Fullero Pyrrolidine]

Fullerene $C_{65}$ (250 mg, 0.35 mmol), N-(4-hydroxyphenyl) glycin (585 mg, 3.50 mmol), pentanal (151 mg, 1.75 mmol) and chlorobenzene (100 mL) were placed in a 200-mL double-necked flask equipped with Gimroth condenser, and heated to reflux for 3 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator. The product was reprecipitated with methanol (50 mL) to form a brown solid (90 mg).

The brown solid was subjected to IR absorption spectrum measurement, LC-MS and element analysis. The results are as follows.

IR Absorption Spectrum Measurement (KBr Tablet Method)
An absorption of OH stretching oscillation was observed at 3,440 $cm^{-1}$
LC-MS (Developing Solvent: Toluene)
m/z=911.89 (theoretical value: 911.91)
Element Analysis
C=94.8% (theoretical value: 94.83%)
H=1.8% (theoretical value: 1.88%)
N=1.6% (theoretical value: 1.54%)

From the above, the brown solid was found to be fullero pyrrolidine having the following formula (2) (yield rate 28.4%):

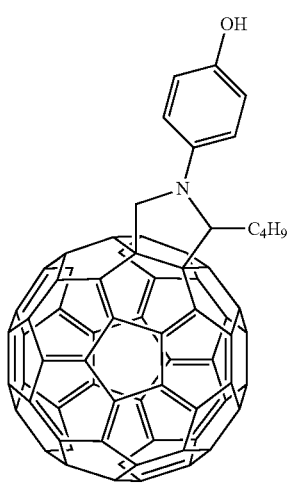

(2)

[Step 2; Synthesis of the Fullerene Derivative No. 6 in Table 1 (One Structural Unit Having the Formula (I)]

The fullero pyrrolidine (100 mg, 0.11 mmol), di-tert-butyl dicarbonate (240 mg, 1.10 mmol), 4-dimethylaminopyridine (130 mg, 1.06 mmol) and pyridine (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator. The product was reprecipitated with methanol (50 mL) to form a brown solid (80 mg).

The brown solid was subjected to IR absorption spectrum measurement, LC-MS and element analysis. The results are as follows.

IR Absorption Spectrum Measurement (KBr Tablet Method)
The absorption of OH stretching oscillation was observed at 3,440 $cm^{-1}$ disappeared, an absorption of C—H stretching oscillation and an absorption of C=O stretching oscillation were observed at 2,920 $cm^{-1}$ and 1,750 $cm^{-1}$, respectively.
LC-MS (Developing Solvent: Toluene)
m/z=1,202.21 (theoretical value: 1,012.03)
Element Analysis
C=91.2% (theoretical value: 91.38%)
H=2.3% (theoretical value: 2.49%)
N=1.5% (theoretical value: 1.38%)

From the above, the brown solid was found to be a fullerene derivative No. 6 having the following formula (2a) (yield rate 65.7%):

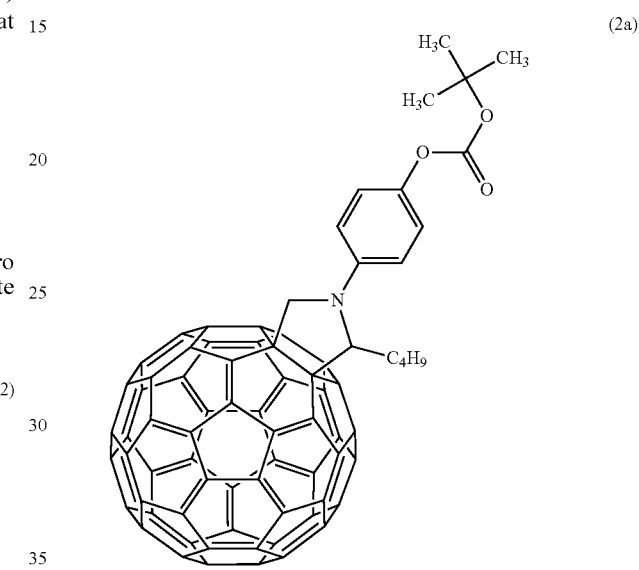

(2a)

Example 3

Synthesis Example of the Fullerene Derivative No. 7 in Table 1 (One Structural Unit Having the Formula (I)

[Step 1; Synthesis of Fullero Pyrrolidine]

Fullerene $C_{60}$ (250 mg, 0.35 mmol), N-(4-hydroxyphenyl) glycin (585 mg, 3.50 mmol), trimethylacetoaldehyde (151 mg, 1.75 mmol) and o-dichlorobenzene (100 mL) were placed in a 200-mL double-necked flask equipped with Gimroth condenser, and heated to reflux for 3 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator. The product was reprecipitated with methanol (50 mL) to form a brown solid (50 mg).

The brown solid was subjected to IR absorption spectrum measurement, LC-MS and element analysis. The results are as follows.

IR Absorption Spectrum Measurement (KBr Tablet Method)
An absorption of OH stretching oscillation was observed at 3,440 $cm^{-1}$
LC-MS (Developing Solvent: Toluene)
m/z=911.77 (theoretical value: 911.91)

Element Analysis

C=94.7% (theoretical value: 94.83%)

H=1.6% (theoretical value: 1.88%)

N=1.6% (theoretical value: 1.54%)

From the above, the brown solid was found to be fullero pyrrolidine having the following formula (3) (yield rate 15.8%):

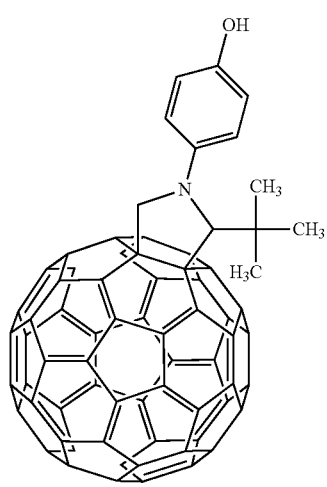

(3)

[Step 2; Synthesis of the Fullerene Derivative No. 7 in Table 1 (One Structural Unit Having the formula (I)]

The fullero pyrrolidine (100 mg, 0.11 mmol), di-tert-butyl dicarbonate (240 mg, 1.10 mmol), 4-dimethylaminopyridine (130 mg, 1.06 mmol) and pyridine (100 mL) were placed in a 200-mL double-necked flask equipped with Gimroth condenser, and stirred for 3 his at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator. The product was reprecipitated with methanol (50 mL) to form a brown solid (70 mg).

The brown solid was subjected to IR absorption spectrum measurement, LC-MS and element analysis. The results are as follows.

IR Absorption Spectrum Measurement (KBr Tablet Method)

The absorption of OH stretching oscillation was observed at 3,440 cm$^{-1}$ disappeared, an absorption of C—H stretching oscillation and an absorption of C=O stretching oscillation were observed at 2,920 cm$^{-1}$ and 1,750 cm$^{-1}$, respectively.

LC-MS (Developing Solvent: Toluene)

m/z=1,012.18 (theoretical value: 1,012.03)

Element Analysis

C=91.3% (theoretical value: 91.38%)

H=2.5% (theoretical value: 2.49%)

N=1.4% (theoretical value: 1.38%)

From the above, the brown solid was found to be a fullerene derivative No. 7 having the following formula (3a) (yield rate 57.5%):

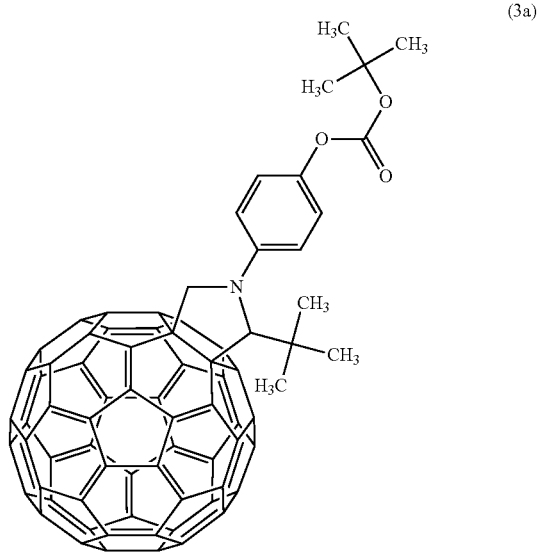 [SMILES: CC(C)(C)OC(=O)Oc1ccc(N2CC34C5=c6c7c8c9c%10c%11c%12c%13c%14c%15c%16c%17c(c6c(c%16%13)c%117)C3(C2C(C)(C)C)C2C%173CC26c2c7c%11c%13c%16c2c2c%17c%18c%19c%20c%21c%22c%23c(c-%13c%21c%18%16)C(C%14C%23C%12C%10C%22C%20C9C9C8C5C(C%17C%199)C4C26)C%11C%15C73)cc1]

(3a)

Example 4

Synthesis Example of the Fullerene Derivative No. 14 in Table 1 (One Structural Unit Having the Formula (I)

[Step 1; Synthesis of Fullero Pyrrolidine]

Fullerene C$_{60}$ (250 mg, 0.35 mmol), N-(4-hydroxyphenyl) glycin (585 mg, 3.50 mmol), decanal (275 mg, 1.76 mmol) and chlorobenzene (100 mL) were placed in a 200-mL double-necked flask equipped with Gimroth condenser, and heated to reflux for 3 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator. The product was reprecipitated with methanol (50 mL) to form a brown solid (110 mg).

The brown solid was subjected to IR absorption spectrum measurement, LC-MS and element analysis. The results are as follows.

IR Absorption Spectrum Measurement (KBr Tablet Method)

An absorption of OH stretching oscillation was observed at 3,440 cm$^{-1}$

LC-MS (Developing Solvent: Toluene)

m/z=982.04 (theoretical value: 982.04)

Element Analysis

C=94.1% (theoretical value: 94.17%)

H=2.6% (theoretical value: 2.77%)

N=1.6% (theoretical value: 1.43%)

From the above, the brown solid was found to be fullero pyrrolidine having the following formula (4) (yield rate 32.3%):

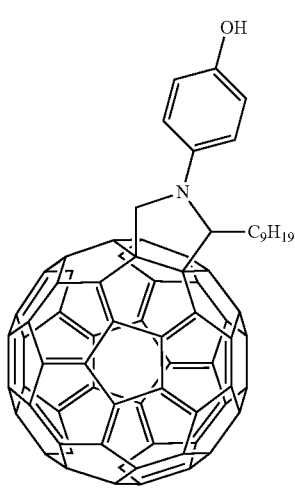

(4)

[Step 2; Synthesis of the Fullerene Derivative No. 14 in Table 1 (One Structural Unit Having the formula (I)]

The fullero pyrrolidine (100 mg, 0.11 mmol), di-tert-butyl dicarbonate (240 mg, 1.10 mmol), 4-dimethylaminopyridine (130 mg, 1.06 mmol) and pyridine (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator. The product was reprecipitated with methanol (50 mL) to form a brown solid (70 mg).

The brown solid was subjected to IR absorption spectrum measurement, LC-MS and element analysis. The results are as follows.

IR Absorption Spectrum Measurement (KBr Tablet Method)

The absorption of OH stretching oscillation was observed at 3,440 cm$^{-1}$ disappeared, an absorption of C—H stretching oscillation and an absorption of C=O stretching oscillation were observed at 2,920 cm$^{-1}$ and 1,750 cm$^{-1}$, respectively.

LC-MS (Developing Solvent: Toluene)

m/z=1,082.00 (theoretical value: 1,082.16)

Element Analysis

C=91.0% (theoretical value: 91.01%)
H=3.1% (theoretical value: 3.26%)
N=1.3% (theoretical value: 1.29%)

From the above, the brown solid was found to be a fullerene derivative No. 14 having the following formula (4a) (yield rate 63.5%):

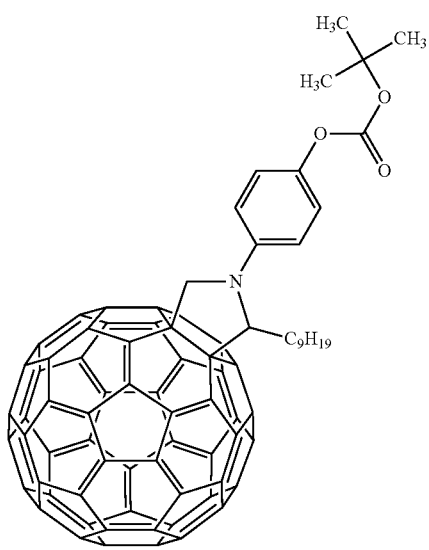

(4a)

Example 5

Synthesis Example of the Fullerene Derivative No. 17 in Table 1 (One Structural Unit Having the Formula (I)

[Step 1; Synthesis of Fullero Pyrrolidine]

Fullerene $C_{60}$ (250 mg, 0.35 mmol), N-(4-hydroxyphenyl) glycin (585 mg, 3.50 mmol), tridecanal (350 mg, 1.76 mmol) and chlorabenzene (100 mL) were placed in a 200-mL double-necked flask equipped with Gimroth condenser, and heated to reflux for 3 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator. The product was reprecipitated with methanol (50 mL) to form a brown solid (100 mg).

The brown solid was subjected to IR absorption spectrum measurement, LC-MS and element analysis. The results are as follows.

IR Absorption Spectrum Measurement (KBr Tablet Method)

An absorption of OH stretching oscillation was observed at 3,440 cm$^{-1}$

LC-MS (Developing Solvent: Toluene)

m/z=1,024.08 (theoretical value: 1,024.12)

Element Analysis

C=94.1% (theoretical value: 93.82%)
H=3.3% (theoretical value: 3.25%)
N=1.5% (theoretical value: 1.37%)

From the above, the brown solid was found to be fullero pyrrolidine having the following formula (5) (yield rate 28.1%):

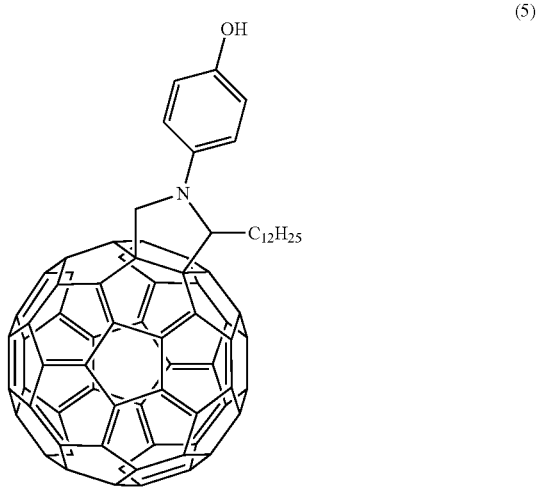

(5)

[Step 2; Synthesis of the Fullerene Derivative No. 17 in Table 1 (One Structural Unit Having the Formula (I)]

The fullero pyrrolidine (100 mg, 0.11 mmol), di-tert-butyl dicarbonate (240 mg, 1.10 mmol), 4-dimethylaminopyridine (130 mg, 1.06 mmol) and pyridine (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator. The product was reprecipitated with methanol (50 mL) to form a brown solid (80 mg).

The brown solid was subjected to IR absorption spectrum measurement, LC-MS and element analysis. The results are as follows.

IR Absorption Spectrum Measurement (KBr Tablet Method)

The absorption of OH stretching oscillation was observed at 3,440 cm$^{-1}$ disappeared, an absorption of C—H stretching oscillation and an absorption of C=O stretching oscillation were observed at 2,920 cm$^{-1}$ and 1,750 cm$^{-1}$, respectively.

LC-MS (Developing Solvent: Toluene)
m/z=1,123.24 (theoretical value: 1,124.24)

Element Analysis
C=91.2% (theoretical value: 90.81%)
H=3.5% (theoretical value: 3.68%)
N=1.4% (theoretical value: 1.25%)

From the above, the brown solid was found to be a fullerene derivative No. 17 having the following formula (5a) (yield rate 72.9%):

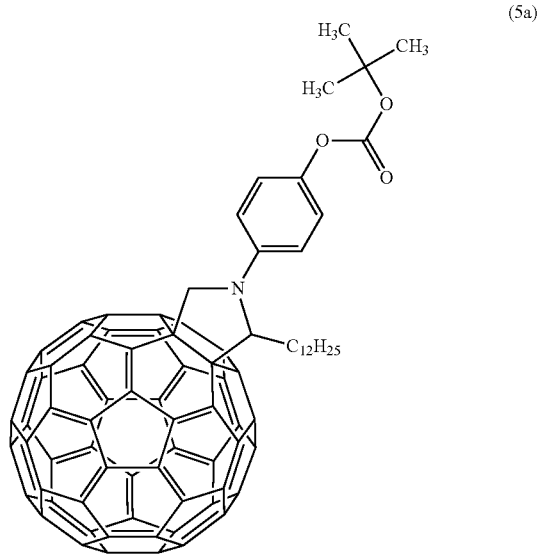

(5a)

Next, the fullerene derivative of the present invention was decarboesterified using a heating means for the purpose of controlling solubility thereof. Application examples follow.

Application Example 1

The fullerene derivative having the formula (1a) in Example 1 (100 mg) was heated at 250° C. for 1 hr on a desktop muffle furnace (KDF-007EX) to form a brown solid (75 mg).

The brown solid was subjected to IR absorption spectrum measurement, LC-MS and element analysis. The results are as follows.

IR Absorption Spectrum Measurement (KBr Tablet Method)
An absorption of OH stretching oscillation was observed at 3,440 cm$^{-1}$ LC-MS (Developing Solvent: Toluene)
m/z=855.78 (theoretical value: 855.81)

Element Analysis
C=95.5% (theoretical value: 95.43%)
H=1.1% (theoretical value: 1.06%)
N=1.7% (theoretical value: 1.64%)

From the above, the brown solid was found to be the fullero pyrrolidine having the following formula (1) in Example 1.

Application Example 2

The fullerene derivative having the formula (2a) in Example 2 (100 mg) was heated by the same method in Example 1 to form a brown solid (80 mg).

The brown solid was subjected to IR absorption spectrum measurement, LC-MS and element analysis. The results are as follows.

IR Absorption Spectrum Measurement (KBr Tablet Method)
An absorption of OH stretching oscillation was observed at 3,440 cm$^{-1}$ LC-MS (Developing Solvent: Toluene)
m/z=911.91 (theoretical value: 911.91)

Element Analysis
C=94.9% (theoretical value: 94.83%)
H=1.9% (theoretical value: 1.88%)
N=1.7% (theoretical value: 1.54%)

From the above, the brown solid was found to be the fullero pyrrolidine having the following formula (2) in Example 2.

Application Example 3

The fullerene derivative having the formula (3a) in Example 3 (100 mg) was heated by the same method in Example 1 to form a brown solid (80 mg).

The brown solid was subjected to IR absorption spectrum measurement, LC-MS and element analysis. The results are as follows.

IR Absorption Spectrum Measurement (KBr Tablet Method)
An absorption of OH stretching oscillation was observed at 3,440 cm$^{-1}$ LC-MS (Developing Solvent: Toluene)
m/z=911.80 (theoretical value: 911.91)

Element Analysis
C=94.8% (theoretical value: 94.83%)
H=1.9% (theoretical value: 1.88%)
N=1.5% (theoretical value: 1.54%)

From the above, the brown solid was found to be the fullero pyrrolidine having the following formula (3) in Example 3.

Application Example 4

The fullerene derivative having the formula (4a) in Example 4 (100 mg) was heated by the same method in Example 1 to form a brown solid (90 mg).

The brown solid was subjected to IR absorption spectrum measurement, LC-MS and element analysis. The results are as follows.

IR Absorption Spectrum Measurement (KBr Tablet Method)
An absorption of OH stretching oscillation was observed at 3,440 cm$^{-1}$ LC-MS (Developing Solvent: Toluene)
m/z=982.00 (theoretical value: 982.04)

Element Analysis
C=94.2% (theoretical value: 94.17%)=
H=2.8% (theoretical value: 2.77%)
N=1.5% (theoretical value: 1.43%)

From the above, the brown solid was found to be the fullero pyrrolidine having the following formula (4) in Example 4.

Application Example 5

The fullerene derivative having the formula (5a) in Example 5 (100 mg) was heated by the same method in Example 1 to form a brown solid (90 mg).

The brown solid was subjected to IR absorption spectrum measurement, LC-MS and element analysis. The results are as follows.

IR Absorption Spectrum Measurement (KBr Tablet Method)
An absorption of OH stretching oscillation was observed at 3,440 $cm^{-1}$ LC-MS (Developing Solvent: Toluene)
m/z=1,024.21 (theoretical value: 1,024.12)

Element Analysis
C=93.9% (theoretical value: 93.82%)
H=3.2% (theoretical value: 3.25%)
N=1.3% (theoretical value: 1.37%)

From the above, the brown solid was found to be the fullero pyrrolidine having the following formula (5) in Example 5.

Solubilities of the fullerene derivatives having the formulae (1a) to (5a) of the present invention in Examples 1 to 5 and the fullero pyrrolidine in Application Examples 1 to 5 in o-dichlorobenzene were evaluated by the following method. A 0.1 mM o-dichlorobenzene solution and a 1.0 mM o-dichlorobenzene solution of each of the fullerene derivatives and the fullero pyrrolidine were prepared, and diluted fivefold with THF for HPLC. Ten (10) μL of the diluted solution was analyzed by a high-speed liquid chromatograph (LC-2010HT from Shimadzu Corp.; developing solvent: THF/ion-exchanged water=60/40; analysis time: 60 min; and detection wavelength: 254 nm) to prepare a chromatogram. Standard curves of the known concentrations (0.1 mM and 1.0 mM) were obtained therefrom. Next, a saturated o-dichlorobenzene solution of each of the fullerene derivatives and the fullero pyrrolidine were prepared at 25° C. After the saturated solution was filtered with a 0.45 μm filter, it was diluted hundredfold with THF for HPLC. Ten (10) μL of the diluted solution was analyzed by the same method mentioned above to prepare a chromatogram. A weight of the fullerene derivative dissolved in 1 mL of o-dichlorobenzene was determined as solubility using a peak area value of the chromatogram from the saturated solution and the standard curves. The results are shown in Table 2.

TABLE 2

| | Weight of the fullerene derivative dissolved in 1 mL of o-dichlorobenzene (mg) |
|---|---|
| Sample having the formula (1a) in Example 1 | 68 |
| Sample having the formula (2a) in Example 2 | 72 |
| Sample having the formula (3a) in Example 3 | 107 |
| Sample having the formula (4a) in Example 4 | 159 |
| Sample having the formula (5a) in Example 5 | 280 |
| Sample having the formula (1) in Application Example 1 | 6 |
| Sample having the formula (2) in Application Example 2 | 20 |
| Sample having the formula (3) in Application Example 3 | 23 |
| Sample having the formula (4) in Application Example 4 | 137 |

TABLE 2-continued

| | Weight of the fullerene derivative dissolved in 1 mL of o-dichlorobenzene (mg) |
|---|---|
| Sample having the formula (5) in Application Example 5 | 238 |

Table 2 proves the solubility of the fullerene derivative decreases with a heating means mentioned in each of the Application Examples.

Application Example 6

Finally, an example of an organic solar battery as an application of the fullerene derivative of the present invention. On a washed and patterned glass plate with an ITO electrode, a solution in which 2 g of PEDOT/PSS[poly(3,4-ethyleneoxythiophene)/poly(styrenesulfonate)] (CLEVIOS PH500 from H.C.Starck GmbH) and 5 g of 2-propanol are mixed was coated by a spin coating method at 1100 rpm, and the coated glass plate was heated on a hot plate at 140° C. for 10 min to form a 40 nm thick positive hole takeout layer thereon. Next, 1.4 g of orthodichlorobenzene, 15 mg of P3HT (LT-S909 from Luminescense Technology Corp.) and 15 mg of the fullerene derivative having the formula (2a) which is refined and isolated by HPLC (developing solvent: chloroform) were stirred a 50° C. for 12 hrs in a nitrogen atmosphere to prepare a coating liquid. On the coated glass plate, the coating liquid was coated by a spin coating method at 800 rpm, and the coated glass plate was heated on a hot plate at 230° C. for 30 min to form a 200 nm thick mixed layer thereon. The thus prepared glass plate was set in a vacuum evaporator to evaporate a 40 nm thick aluminum electrode thereon to prepare an organic solar battery.

Light having 100 $mW/cm^2$ intensity was emitted from a solar simulator (AM1.5G filter) to the organic solar battery, a mask having an effective area of 0.16 $cm^2$ was overlapped on a light receiver, and a current-voltage property between the ITO electrode and the aluminum electrode was measured by a solar battery evaluation system (As-510-PV from NF Corp.) to determine an exchange efficiency. The exchange efficiency was 1.35%, which proves the fullerene derivative of the present invention realizes high exchange efficiency in an organic solar battery.

Having now fully described the invention, it will be apparent to one of ordinary skill in the art that many changes and modifications can be made thereto without departing from the spirit and scope of the invention as set forth therein.

What is claimed is:

1. A fullerene derivative having 60 or more carbon atoms and at least one structure having the following formula (I):

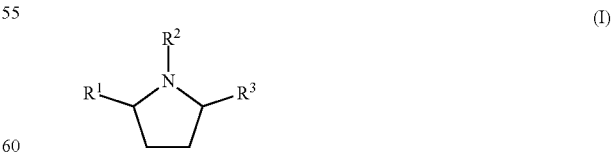

wherein $R^1$, and $R^3$ independently represent a hydrogen atom, a halogen atom, a substituted or unsubstituted alkyl group, a substituted or unsubstituted alkoxy group, a substituted or unsubstituted aryl group or a substituted or unsubstituted monofunctional heterocyclic group; and wherein $R^2$ has the following formula (IV):

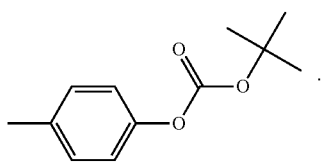
(IV)

2. A method of preparing a fullerene derivative having 60 or more carbon atoms and at least one structure having the following formula (I):

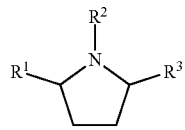
(I)

wherein $R^1$, and $R^3$ independently represent a hydrogen atom, a halogen atom, a substituted or unsubstituted alkyl group, a substituted or unsubstituted alkoxy group, a substituted or unsubstituted aryl group or a substituted or unsubstituted monofunctional heterocyclic group; and wherein $R^2$ has the following formula (IV):

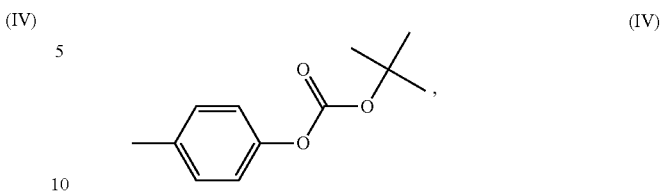
(IV)

comprising:
reacting fullerene, a glycin derivative, and an aldehyde derivative, with diethylpyrocarbonate having the following formula (V) to obtain the fullerene derivative:

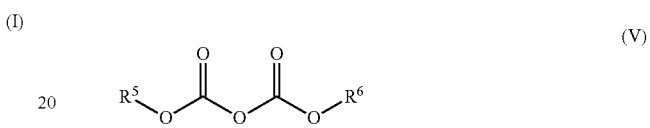
(V)

wherein $R^5$ and $R^6$ independently represent a substituted or unsubstituted alkyl group having 4 to 30 carbon atoms, a substituted or unsubstituted alkenyl group having 4 to 30 carbon atoms, a substituted or unsubstituted alkynyl group having 4 to 30 carbon atoms or a substituted or unsubstituted aralkyl group having 4 to 30 carbon atoms.

* * * * *